United States Patent [19]

Duquet et al.

[11] Patent Number: 5,543,209
[45] Date of Patent: Aug. 6, 1996

[54] SURFACE COATING FOR PROSTHESIS SYSTEM CONTAINING HA/TCP COMPOSITION

[75] Inventors: Bruno Duquet, Lille; Guy Daculsi, Vigneux De Bretagne; Joël Delecrin, Nantes, all of France

[73] Assignee: Zimmer, Inc., Warsaw, Ind.

[21] Appl. No.: 532,906

[22] Filed: Sep. 22, 1995

Related U.S. Application Data

[63] Continuation of Ser. No. 226,095, Apr. 11, 1994, abandoned, which is a continuation of Ser. No. 26,917, Mar. 5, 1993, abandoned.

[30] Foreign Application Priority Data

Mar. 6, 1992 [FR] France .................................. 92 02702

[51] Int. Cl.$^6$ ................................ B32B 7/02; B32B 9/04
[52] U.S. Cl. .......................... 428/212; 106/35; 106/286.6; 106/286.8; 106/287.29; 428/215; 428/220; 428/310.5; 428/701; 428/702; 428/704; 623/11; 623/16
[58] Field of Search ........................... 428/212, 215, 428/220, 310.5, 323, 701, 702, 704, 333, 334; 623/11, 16; 106/35, 286.1, 286.6, 286.8, 287.29

[56] References Cited

U.S. PATENT DOCUMENTS

| | | | |
|---|---|---|---|
| 4,097,935 | 7/1978 | Jarcho | 3/1.9 |
| 4,103,002 | 7/1978 | Hench et al. | 428/155 |
| 4,146,936 | 4/1979 | Aoyagi et al. | 3/1.91 |
| 4,338,926 | 7/1982 | Kummer et al. | 128/92 BC |
| 4,542,539 | 9/1985 | Rowe et al. | 623/16 |
| 4,599,085 | 7/1986 | Riess et al. | 623/16 |
| 4,917,702 | 4/1990 | Scheicher et al. | 623/16 |
| 5,034,352 | 7/1991 | Vit et al. | 501/1 |
| 5,071,434 | 12/1991 | Tsuzuki et al. | 623/16 |
| 5,139,424 | 8/1992 | Yli-Urpo | 433/201.1 |
| 5,152,791 | 10/1992 | Hakamatsuka | 623/16 |
| 5,171,326 | 12/1992 | Ducheyne et al. | 623/66 |

FOREIGN PATENT DOCUMENTS

| | | | |
|---|---|---|---|
| 0371491A1 | 11/1989 | European Pat. Off. | A61L 27/00 |
| 4020598A1 | 6/1990 | Germany | A61L 27/00 |
| 63-160665 | 7/1988 | Japan | A61L 27/00 |
| 63-160666 | 7/1988 | Japan | A61L 27/00 |
| PCT 86/06617 | 11/1986 | WIPO | A61F 2/30 |

*Primary Examiner*—Dhirajlal Nakarani
*Assistant Examiner*—H. Thi Le
*Attorney, Agent, or Firm*—Todd A. Dawson

[57] ABSTRACT

The coating for a prothesis system has a resorbability gradient in the direction perpendicular to the surface of the prothesis system, the internal layer being the least resorbable. It can consist of phospho-calcium material or of two or several successive layers having different resorbabilities and having said resorbability gradient. The prothesis systems covered with the coating according to the invention are used in surgery for the provision of thigh-bone protheses as well as protheses for the facial, ear, nose and throat surgery and the like.

13 Claims, No Drawings

SURFACE COATING FOR PROSTHESIS SYSTEM CONTAINING HA/TCP COMPOSITION

This application is a continuation of application Ser. No. 08/226,095 filed Apr. 11, 1994 abandoned which is a continuation of application Ser. No. 08/026,917 filed Mar. 5, 1993 abandoned.

FIELD OF THE INVENTION

The present invention relates to a novel surface coating for a prothesis system and to prothesis systems covered with this present coating.

BACKGROUND OF THE INVENTION

Protheses or prothesis systems are being used more and more in the field of surgery. For example, typical applications concern the use in orthopedics of thighbone and hip protheses in the case of a fracture of the neck of the thighbone, arthritis of the hip, protheses for reparatory facial plastics surgery, orthopedics and other applications.

Like any foreign body introduced into the human or animal organism, the prothesis system needs to get integrated by the organism, and must also fulfill the functions of the deficient or replaced organ, in a manner which is fast, reliable, and durable.

So-called bio-compatible materials that are currently used for producing such prothesis systems for implant purposes are ceramics, Co—Cr—Mo alloys, and, currently, above all, titanium and alloys thereof. Thanks to the use of such bio-compatible materials, the bone prothesis system is only very slightly subject to the phenomenon of reject. Nevertheless, specific problems have occurred. Effectively, since these bone prothesis systems are implanted into a bone; for example, when a thigh bone prothesis is implanted into the intramedullary passage, it is necessary, in order for the prothesis system to be able to fulfill its functions effectively, rapidly, reliably, and durably, that fast, reliable, and durable growth of the bone take place at the interface around this prothesis system followed by subsequent bone bonding thereof. Thus, surface coatings for prothesis systems have been proposed, the function of which is to promote said growth or bone response at the bone/prothesis interface in order to lead to osseous accretion and to an osteo-integration, this being required to take place speedily, reliably, and durably.

Numerous surface coatings have been proposed, and those which have been adopted to date are based on calcium phosphate. Effectively, bone contains a major proportion of calcium phosphate and it would hence be natural to employ this for surface coatings as its nature and chemical structures are similar to those of bone. The various calcium phosphates are hydroxyapatite (HA), tricalcium phosphate (TCP) in its α and β form (α-TCP and β-TCP respectively) and several other calcium phosphates. These calcium phosphates differ from each other by their stoechiometry and their crystallographic properties. The calcium phosphate which currently comes closest to the osseous type is hydroxyapatite. The latter compound is now widely employed as a coating material for prothesis systems applied in thicknesses varying from several tens to several hundreds of μm. Compounds such as TCP and mixtures thereof with HA are also employed along with other phosphates of calcium.

Unfortunately, as bone growth is an extremely complex phenomenon, present day phospho-calcium coatings for protheses do not currently provide complete satisfaction. Bone growth can be divided into two major reactions: a chemical reaction and a histological reaction.

The histological reaction firstly comprises a "cleaning up" stage carried out with the aid of the macrophages which clean up the surface of the implant by phagocytosis.

Following this, the histological reaction continues through colonization of the surface coating by cells, such as osteoblasts, fibroblasts, the previously mentioned macrophages etc., and by extra-cellular liquid. Colonization of the coating surfaces takes place. The extra-cellular components contain, among other things, proteinaceous fibers, such as collagen fibers. When the matrix settles down and is principally made up of collagen fibers, it is then highly differentiated and constitutes an osteoid.

The chemical reaction consists firstly of an extra-cellular dissolution. The solution comprised in the surface coating becomes enriched in calcium and phosphorous ions, released by the dissolving out of certain crystals. Following this, the released and dissolved ions precipitate. Such precipitation takes place in the extra-cellular fluid, this being a medium rich in proteins onto which the ions become fixed. The thus formed crystals take the form of needle-shaped crystals of biological apatites identical to those of bone. When the proteinaceous matrix is an osteoid, ion precipitation leads to osteocoalescence between the host tissue and the surface of the material of the prothesis. Osteo-genesis at the surface of the thus obtained surface coating is characterized by true bone affixed to the surface of the bioactive material constituting the prothesis.

Various coatings have been proposed and the one that is most frequently used is HA. This coating, however, suffers from the disadvantage of only being reabsorbable very slowly and of only being slightly bioactive. Certain authors have described HA as being a nonresorbable material, meaning that breakdown through the dissolving/precipitation process is very slow and, moreover, HA does not encourage mineralization on the collagen matrix, which is the ultimate aim being sought. Formation and accretion of true bone could be delayed. Coatings that are more bio-reactive than HA, in other words, that are semi-resorbable have been proposed. Among these, TCP is the most bio-reactive. Unfortunately, bio-degradation of TCP sometimes takes place too quickly, with resorption being too high. The osteoid has not yet formed when dissolving/precipitation takes place and hence a bone is not able to form. It seems to be necessary to have a mixed product available which associates the stability of Ha and the high bio-reactivity of TCP, like in applications where a two-phase macroporous material is used for bone filling.

Thus, two-phase HA/TCP or BCP (biphase calcium phosphate) systems have been proposed. BCPs in a 60/40 ratio correspond to the objectives of equilibrium between histological and chemical phenomena. Nevertheless, BCP still suffers from two disadvantages. Since the coating application technique makes use of a plasma torch or electrophoresis associated with a sintering operation, the crystalline form of the TCP can vary between the β and α form, and as α-TCP is more soluble than the β form, the properties of the BCP vary as a consequence. BCP obtained by plasma is hence highly bioactive. In the case of secondary complications, such as loosening of the implant in the receiving bone or septic complications, such complications could lead to the surface of the biocompatible material constituting the prothesis rapidly becoming bare. In this case, short-term fibrous encapsulation takes place and osteo-integration would become impossible.

Thus, there is no currently used coating that allows the above stated aims to be achieved effectively, such objectives requiting accretion and anchoring to the bone to take place rapidly, reliably, and durably.

DESCRIPTION OF THE PREFERRED EMBODIMENTS

The aim of the present invention is hence to provide a novel bioactive coating for a prothesis system having improved breakdown and accretion kinetics.

The present invention hence provides a coating for a prothesis system characterized in that it exhibits a resorbability gradient along the direction perpendicular to the surface of said prothesis system, the internal layer being the least resorbable.

The expression "resorbability" in the present specification means the capacity of a material to undergo resorption (or to break down) by the dissolving/precipitation phenomenon. High resorbability corresponds to fast resorption, and vice versa. The expression "resorbability gradient" means, in this present specification and in the claims attached thereto, a difference, whether this be discrete or continuous, in resorbability between the outer and inner layers, the inner layer being the least resorbable. The internal layer is the layer that is in contact with the biocompatible material that constitutes the prothesis, the outer layer being in contact with the host tissue; in other words, the receiving bone. This difference is of a factor of at least 3, and said difference can be monotonous or not.

Preferably, the coating consists of a phospho-calcium material.

In one embodiment, the coating consists of two or more successive layers of differing resorbability having said resorbability gradient. The difference is discrete in this case.

Advantageously, the coating consists of a layer having high resorbability and a layer having low resorbability.

The said low resorbability layer is preferably a layer in a non-resorbable material; in other words, only very slightly resorbable and feebly bioactive. Advantageously, the non-resorbable material is hydroxyapatite (HA). The said high resorbability layer is preferably a layer in a semi-resorbable material. Advantageously, the semi-resorbable material is a two-phase composition by mass of from 30/70 to 80/20.

In the embodiment in which the present coating consists of two layers, the thickness of said high resorbability layer is from 10 to 100 µm, preferably from 20 to 50 µm. In this same embodiment, the thickness of said low resorbability layer is from 1 to 40 µm, preferably from 1 to 10 µm.

The present invention also relates to any prothesis system covered with the present coating. The prothesis system can be a femur prothesis, a facial prothesis, etc. The coating according to the present invention is applied by any conventional means such as electrophoresis with sintering, or with the aid of a plasma torch.

The following examples are provided by way of non-limiting illustrations of the present invention which may itself be subject to variations readily accessible to those skilled in the art.

EXAMPLE

The properties were evaluated using a statistical study carded out on sample test specimens in the form of small cylindrical sticks subjected to axial extraction testing and to histological section analysis.

Coatings and surfaces tested

Tr: control, the coating of which undergoes resorption (Ra: 2.2)

Ts: control having a glass ball jet-blasted surface state (Ra: 0.7)

HA: 100% hydroxyapatite +3% (impurities) (50 µm)

BCP: two-phase system: 60% HA/40% TCP (50 µm)

RS: coating according to the present invention:
 -HA 100%+3%, 30 µm
 -BCP 60/40, 30 µm The coatings were applied using a plasma torch. Operating conditions were those conventionally employed for a torch under atmospheric conditions. Ra indicates surface roughness as the term is commonly used within the industry.

Test samples

The shape of the test sample was especially designed to facilitate its extraction and implantation. The test sample was cylindrical, 9 mm long and of outer diameter 3.5 mm, carrying an internal circular hollow drilling of 1 mm diameter. The test sample was in TA 6 V titanium (according to ASTM F 620.79).

Implantation of test samples

Each animal of the male sex had the same weight (2.7±0.2 kg) during the first intervention.

Implantation was carried out at two places, the first was located at the upper epiphysary region of the tibia (below the "knee" and in the frontal plane) and the second was located at the lower epiphysary region of the femur (above the "knee" and in the sagittal plane). Surgical implantation was done by internal route, taking care to move the muscular masses in order to allow subsequent coveting. Drilling was done at constant speed, a bit (diameter 3.5 mm) of predetermined length providing depth limitation, and while using constant irrigation. The test sample was then introduced into the drilled hole thus provided. Drilling pressure was checked manually and drilling angle was evaluated visually.

Statistical analysis method 40 rabbits were used for the purposes of analysis. The first intervention consisted in implanting 2 test samples into a rear foot. Three weeks later, the second foot also received 2 implants. Sacrifice took place after 6 weeks thus allowing the 3 and 6 week implants to be recovered from the same rabbit ready for extraction tests and analysis of histological sections. Each type of test sample is represented 6 times in each implantation site and for each duration of implantation. This distribution is summarized in table 1.

TABLE I

| Test Sample | 3 WEEKS | | | | 6 WEEKS | | | | TOTALS | |
|---|---|---|---|---|---|---|---|---|---|---|
| | Femur | | Tibia | | Femur | | Tibia | | | |
| | Histo* | Extraction | Histo | Extraction | Histo | Extraction | Histo | Extraction | Histo | Extraction |
| HA | 1 | 5 | 1 | 5 | 1 | 5 | 1 | 5 | 4 | 20 |
| BCP | 1 | 5 | 1 | 5 | 1 | 5 | 1 | 5 | 4 | 20 |
| RS | 1 | 5 | 1 | 5 | 1 | 5 | 1 | 5 | 4 | 20 |
| Ts | 1 | 5 | 0 | 12 | 0 | 6 | 1 | 11 | 2 | 34 |
| Tr | 0 | 12 | 1 | 5 | 1 | 11 | 0 | 6 | 2 | 34 |
| | | | | | | | | | 16 | 128 |

*histological section

Extraction of test samples

The implants which underwent the extraction tests were operated on as follows:

- bone dissection;
- clearing of the ends of the test samples with a scalpel;
- freezing immediately afterwards in liquid nitrogen;
- fitting of the bones into a test rig;
- extraction of the test samples by backward pushing: The end of a 3.5 mm diameter cylindrical guide part was brought into contact with one end of the test sample;
- measurement of the force required to extract each test sample;
- calculation of the stresses involved after defining the active surface using radiography and employing graduated plates.

The results are given in Mpa in table II below:

TABLE II

| | 3 WEEKS | | 6 WEEKS | |
|---|---|---|---|---|
| | FEMUR | TIBIA | FEMUR | TIBIA |
| HA | 2.760 | 3.053 | 3.025 | 2.439 |
| BCP | 3.214 | 3.251 | 3.199 | 2.582 |
| RS | 4.090 | 3.846 | 3.574 | 5.262 |
| Tr | 2.144 | 3.238 | 2.438 | 2.165 |
| Ts | 0.520 | 0.641 | 0.840 | 1.382 |

These results demonstrate clearly that the extraction force for the coating according to the present invention is distinctly higher than that for conventional coatings.

Histological sections

The implants which underwent histological sectioning were treated as follows:

- euthanasia of the rabbits and immediate dissection;
- clinical observation during dissection of the muscular masses;
- sampling of the femoral segment containing the implants by diamond disc or bone saw sectioning;
- fixation with a gluta-paraformaldehyde mixture;
- X-ray radiography of the samples on standard dental film;
- dehydration of the samples using alcohol of increasing strength;
- inclusion of methyl methacrylate parts using the calcified tissue process;
- oven polymerization;
- diamond disc saw sectioning;
- thinning down with abrasive disc;
- taking of microradiography contact shots on HR film;
- fitting between microscope slides;
- photonic microscopy observation with normal, polarized and blue light for fluorescence test;
- study of a section per implant using a scanning electron microscope and energy dispersion microanalysis of the bone/prothesis interface.

Histological results

Bone regrowth was observed, very frequently going right up to osseous contact. A narrow fibrous border or osteoid separated the bone from the implant. Osseous turnover was observed right from the 6th week.

-Resorbed coating: Tr

The surface condition of these samples was very rough (shot blasted). Bone regrowth seemed better than for powder-blasted titanium, the osteoid fibrous interface was rarely visible. Haversian turnover processes were visible in direct contact with the implant.

-HA coating

The bone response was significant and "short" along the implant from the cortical up to several tens of a nun in the medulla region. Osseous turnover appeared fight from the 3rd week and although osseous contact was perfect, medullary regions in contact with the HA coating continued to exist. In these regions, resorption processes seemed to be appearing, but these were very limited.

-BCP coating

There was very significant osseous regrowth right from the 3rd week, the whole of the implant being covered with bone. In the medulla region, a continuous bone front of thickness 50 to 100 μm was observed which was lamellar in form, well mineralized and rich in osteocytes.

Regions of resorption did appear, and the coating "texture" had changed. Under polarized light and powerful enlargement, infiltration by components of the organic matrix and a mineral transformation appeared to have taken place, pores being visible (several microns in diameter).

After 6 weeks, the osseous density had increased and numerous osseous rearrangements were observed right up to contact with the BCP. The deposited matter, however, appeared to be very fragile and friable, since numerous artifacts from preparation appeared.

-Sandwich coating: RS

The two layers were not identifiable. Histological examination yielded results identical to those from the test samples that had a BCP coating; however, the artifacts from preparation and from sectioning were less apparent.

The strength of the sandwich coating seemed hence better than that of BCP alone, and similar to that of an HA coating, but, on the other hand, the quality and quantity of osseous regrowth (in particular at the medulla region) was similar to the BCP coating.

The sandwich coating hence makes it possible to:
- develop strong bio-activity and an osteoconduction better than HA;
- maintain a mechanical resistance to stresses which is equivalent to that of conventional HA deposits.

We claim:

1. A phospho-calcium coating for a prosthetic implant comprising at least a first resorbable layer and at least a second resorbable layer, said first layer being more resorbable than the second layer by a factor of at least three, wherein the first layer overlies the side of the second layer opposite to the side closer to the implant, and wherein the second layer is formed from hydroxyapatite and the first layer is formed from a two-phase hydroxyapatite tricalcium phosphate material.

2. The coating of claim 1 wherein the two phase hydroxyapatite tricalcium phosphate material has a mass ratio of hydroxyapatite to tricalcium phosphate of 30/70 to 80/20.

3. The coating of 1 wherein the thickness of the first layer is from 10 to 100 μm.

4. The coating of claim 3 wherein the thickness of the first layer is from 20 to 50 μm.

5. The coating of claim 1 wherein the thickness of the second layer is from 1 to 40 μm.

6. The coating of claim 5 wherein the thickness of the second layer is from 1 to 10 μm.

7. A phospho-calcium coating for a prosthetic system comprising at least a first layer and at least a second layer, said first layer being more resorbable relative to the second layer by a factor of at least three, wherein the first layer overlies the side of the second layer opposite to the side closer to the implant, said second layer being formed from hydroxyapatite and having a thickness of from 1 to 40 μm, the first layer being formed from a two-phase hydroxyapatite tricalcium phosphate material and having a thickness of 10 to 100 μm, said two-phase material having a mass ratio of hydroxyapatite to tricalcium phosphate of 30/70 to 80/20.

8. A prosthetic implant having a coating comprising at least a first layer and at least a second layer, the first layer being more resorbable than the second layer by a factor of at least three, wherein the first layer overlies the side of the second layer opposite from the side closer to the implant, and wherein the second layer is formed from hydroxyapatite and the first layer is formed from a two-phase hydroxyapatite tricalcium phosphate material.

9. The prosthetic implant of claim 8 wherein the two phase hydoxyapatite tricalcium phosphate material has a mass ratio of hydroxyapatite to tricalcium phosphate of 30/70 to 80/20.

10. The prosthetic implant of 8 wherein the thickness of the first layer is from 10 to 100 μm.

11. The prosthetic implant of claim 10 wherein the thickness of the first layer is from 20 to 50 μm.

12. The prosthetic implant of claim 8 wherein the thickness of the second layer is from 1 to 40 μm.

13. The prosthetic implant of claim 12 wherein the thickness of the second layer is from 1 to 10 μm.

\* \* \* \* \*